United States Patent [19]

De-Ambrosi

[11] Patent Number: 5,403,827
[45] Date of Patent: Apr. 4, 1995

[54] PROCESS FOR PREPARING EPOXY-HEPARIDES, THE PRODUCTS OBTAINED AND PHARMACEUTICAL COMPOSITIONS CONTAINING THEM

[75] Inventor: Luigi De-Ambrosi, Santhia', Italy

[73] Assignee: Laboratori Derivati Organici S.p.A., Milan, Italy

[21] Appl. No.: 146,805

[22] Filed: Nov. 2, 1993

Related U.S. Application Data

[63] Continuation of Ser. No. 784,252, Oct. 29, 1991, abandoned.

[30] Foreign Application Priority Data

Oct. 29, 1990 [IT] Italy .......................... 21909

[51] Int. Cl.$^6$ ...................... A61K 31/725; C07H 3/10; C07H 5/06
[52] U.S. Cl. ........................ 514/56; 536/21; 536/54; 536/55; 536/55.1; 536/56
[58] Field of Search .................... 536/21, 54, 55, 55.1, 536/55.3; 514/56

[56] References Cited

U.S. PATENT DOCUMENTS

| 3,179,566 | 4/1965 | Horner et al. ................ 536/21 |
| 4,629,699 | 12/1986 | Bianchini ................ 536/21 |
| 4,727,063 | 2/1988 | Naggi et al. ................ 536/21 |
| 4,791,195 | 12/1988 | Bianchini et al. ................ 536/21 |
| 4,933,326 | 6/1990 | Bianchini et al. ................ 536/21 |
| 4,973,580 | 11/1990 | Mascellani et al. ................ 536/21 |
| 4,981,955 | 1/1991 | Lopez ................ 536/21 |
| 5,010,063 | 4/1991 | Piani et al. ................ 514/54 |

FOREIGN PATENT DOCUMENTS

0165569 12/1985 European Pat. Off. .
0347588 12/1989 European Pat. Off. .

OTHER PUBLICATIONS

Canadian J. Chem, 67(9) 1371-1508 (1989) Jaseja et al.

Schmidt et al; Carbohydrate Research 89:159-162 (1981).
Jaseja et al. Can. J. Chem. 1989, 67(9), 1449-1456.

Primary Examiner—John W. Rollins
Assistant Examiner—Kathleen Kahler Fonda
Attorney, Agent, or Firm—Hedman, Gibson & Costigan

[57] ABSTRACT

There is provided a process for preparing epoxy-heparide polysaccharides of formula (I):

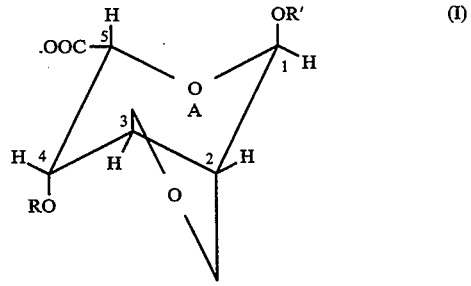

wherein A is a pyran ring with substituents 1 and 4 in the axial position and 5 in the equatorial position, and R and R' are hexosamines which constitute a polysaccharide chain bonded to said ring A by a glucoside, and one of R and R' is H when the ring A is in the terminal position of said polysaccharide chains, and said heparide has a COCH$_3$ to COOH ratio of 0.5, said process comprising a) N-desulfation of heparin to obtain the corresponding heparamine;
b) acetylation of the heparamine of step (a) to obtain the corresponding heparide;
c) epoxidation of the heparide of step (b) by treating the heparide with hydrogen peroxide in an alkaline reaction medium at pH 12–14; and
d) cooling the solution obtained in step (c) to a temperature of between 15° and 25° C. and adjusting the pH to between 5.8 and 6.0.

12 Claims, 1 Drawing Sheet

PROCESS FOR PREPARING EPOXY-HEPARIDES, THE PRODUCTS OBTAINED AND PHARMACEUTICAL COMPOSITIONS CONTAINING THEM

This is a continuation of U.S. Ser. No. 07/784,252, filed Oct. 29, 1991, now abandoned.

PRIOR ART

Heparin is a medicament widely used in anticoagulant treatment, in which however it has the drawback of promoting side reactions associated with thrombocytopenia and hemorrhagic phenomena.

Considerable research has been conducted on modifying the structure of heparin to reduce its side effects.

It has been found for example that low molecular weight (LMW) heparins have reduced anticoagulant power while maintaining their antithrombotic characteristics.

Studies conducted on the desulphation of the heparin amino group have resulted in partially N-desulphated compounds having pharmacological characteristics similar to LMW heparin to the extent of attaining the absence of anticoagulant activity and associated high antithrombotic capacity determined in "in vivo" on rabbits in accordance with the thrombosis-by-stasis model. These compounds also have fibrinolytic activity, which makes them suitable not only for the prophylaxis but also for the therapy of thrombosis.

This group of partially N-desulphated compounds was named "heparamines" by VELLUZ (C.R. Acad. Sci Paris-247, 1521 (1958), and was illustrated by SACHE and Coll. (Thrombosis Res. 55, 247 (1989) and by INDOE and Coll. (Carbohyd. Res. 46, 87 (1976).

A further step in the structural modification of heparamines was achieved by the acetylation of the desulphated amino group to obtain the so-called heparides described by Purkenson and Co. (J. Clin. Invest. 81, 69 (1988), INDUE and Coll. (Carbohyd. Res. 46, 87 (1976) and LYNN and Coll. (Carbohyd. Res. 145, 267 (1986).

Finally, JASEJA (Can J. Chem. 67, 1949 (1989) describes the 2,0-desulphation of heparin iduronylsulphate by heating in an alkaline environment, with the formation of an unstable intermediate (2,3-oxiranic derivative). This intermediate cannot however be isolated because the reaction proceeds with the opening of the epoxide bridge and the formation of the corresponding diol.

SUMMARY OF THE INVENTION

The present invention relates to epoxy-heparides obtained in stable form and having the general formula (I):

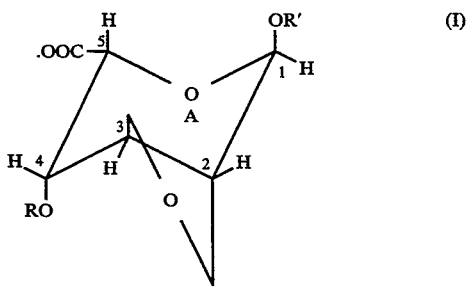

in which A is a pyran ring with substituents 1 and 4 in the axial position and 5 in the equatorial position, and R and R' are hexosamines bonded to the ring A by a glucoside bond, or R and R' are H when the ring A is in the terminal position in the polysaccharide chain or when it is isolated.

Said compositions are obtained by a process comprising:
a) partial N-desulphation of heparin;
b) acetylation of the heparamine;
c) epoxidation of the acetylated heparamine by treatment with hydrogen peroxide in a strongly alkaline reaction medium.

The compounds obtained have high antithrombotic and fibrinolytic activity with absence of anticoagulant activity.

The invention therefore also relates to the use of said derivatives in the preparation of pharmaceutical compositions for antithrombotic and fibrinolytic treatment.

DETAILED DESCRIPTION OF THE INVENTION

The characteristics of the process for preparing epoxy-heparides according to the invention and the characteristics, advantages and uses of the compounds obtained will be more apparent from the following detailed description.

Said compositions have the following general formula (I):

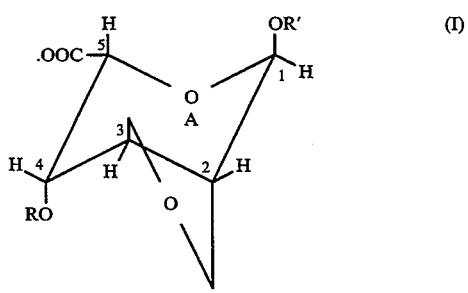

in which A is a pyran ring with substituents 1 and 4 in the axial position and 5 in the equatorial position, and R and R' are hexosamines bonded to the ring A by a glucoside bond, or R and R' are H when the ring A is in the terminal position in the polysaccharide chain or when it is isolated.

The process of the present invention is implemented in there stages a), b) and c), as represented in the following Scheme 1.

Scheme 1:

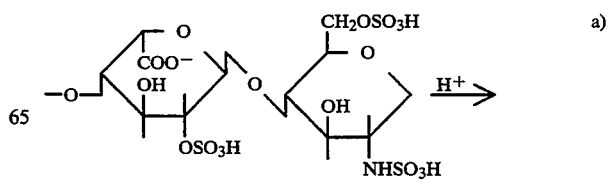

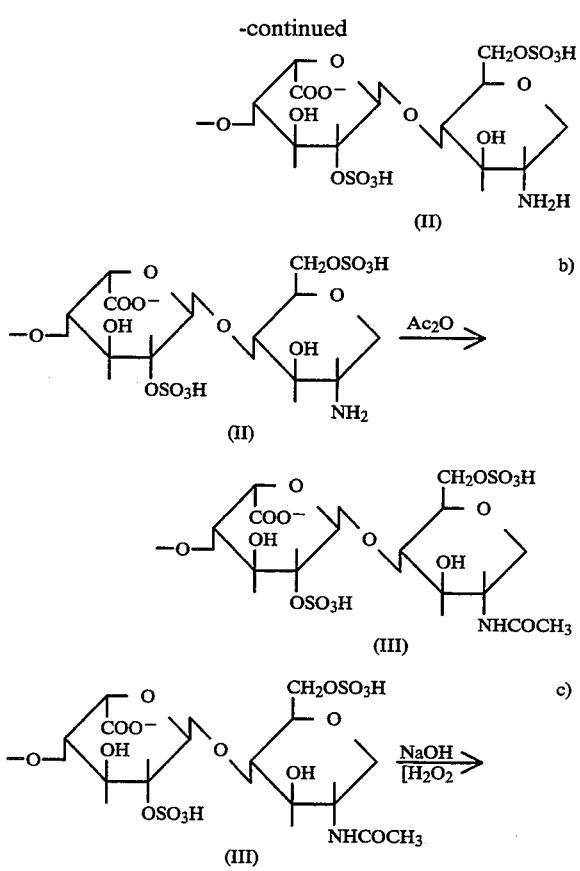

NaOH, KOH or NH$_4$OH can be used as the alkaline substance.

37% hydrogen peroxide in a quantity of between 0.5 and 1 ml per 10 g of heparide (III) is added in small portions over a period of 1–4 hours.

During this addition, the temperature is maintained between 40° and 80° C., and at the end of the operation the solution is cooled rapidly to a temperature of between 15° and 25° C.

The pH is then corrected to between 5.8 and 6.0.

The solution is then subjected to desalification either by ultrafiltration or by treatment with resins, the product finally being precipitated by treating the solution with an equal volume of hydrophilic solvents such as acetone, ethanol or methanol.

The precipitate is then dried, redissolved in distilled water and depyrogenated, and at this point is treated by a suitable method to obtain the form required for the composition for which it is intended. For example, it can be lyophilized for use in injectable compositions or spray-dried for use in oral compositions.

Under the described conditions the epoxy derivative forms within the polymer without the structure undergoing depolymerization and without undergoing the β-elimination reaction with the formation of double bonds.

The substituent in the axial (more reactive) 2 position in the $^1C_4$ structure, typical of L-iduronic acid, favours the formation of an epoxide bridge between the C$_2$ and C$_3$ substituents, which does not happen for the unsubstituted $^4C_1$ structures typical of D-glucronic acid.

Depending on the environmental conditions and compatibility with the adjacent bonds, the epoxide thus formed can subsequently stabilize in conformer equilibrium with forms of $^4C_1$ and $^2S_0$ type as shown in Scheme 2.

Scheme 2:

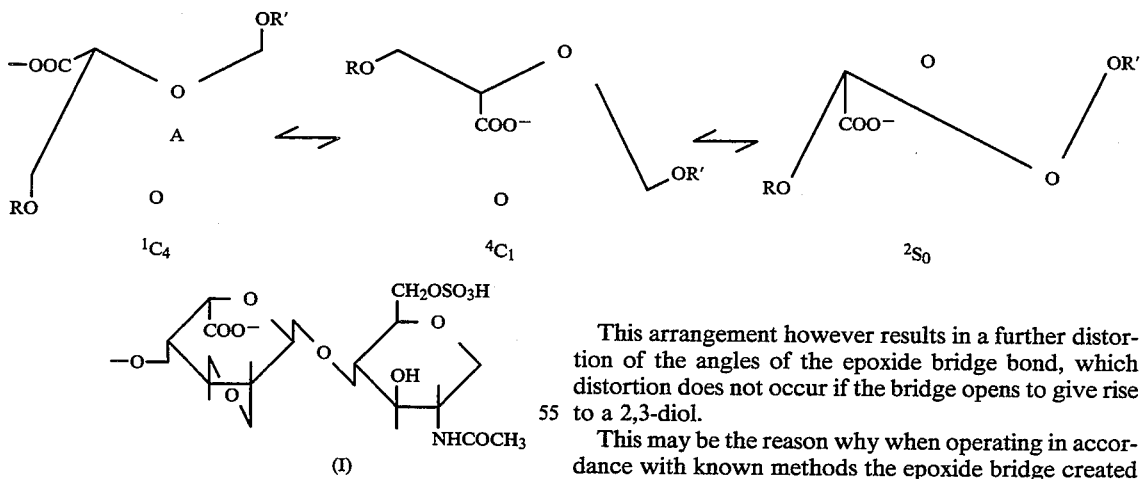

Stages a) and b) are conducted in known manner.

Specifically, in stage a) the heparin is treated with an aqueous HCl solution to desulphate the amino group, whereas in stage b) the heparamine (II) obtained from stage a) is treated with acetic anhydride in slightly alkaline solution to obtain the acetylated product (III) (heparide).

In stage c) the heparide (III) is dissolved in an aqueous alkaline solution at pH 12–14 at a temperature of between 40° and 80° C.

This arrangement however results in a further distortion of the angles of the epoxide bridge bond, which distortion does not occur if the bridge opens to give rise to a 2,3-diol.

This may be the reason why when operating in accordance with known methods the epoxide bridge created is unstable and evolves into open forms.

In contrast under the conditions of the process according to the invention the epoxide can be isolated in stable form in that the operative parameters of the invention lead to the maximum formation of the epoxy derivative and prevent the opening of the ring, the formation of double bonds and depolymerization.

The chemical characteristics of the intermediate compounds and of the final compound of the invention, as obtained in Example 1 described hereinafter, are shown in Tables 1 and 2, in which:

Compound 1 = sodium heparin
Compound 2 = partially N-desulphated heparin (heparamine)
Compound 3 = partially N-desulphated and acetylated heparin (heparide)
Compound 4 = epoxy derivative (epoxy-heparide)

TABLE 1

| Compound | Specific rotation | $SO_3H$ COOH | $COCH_3$ COOH | MW $\times 10^3$ | S % |
|---|---|---|---|---|---|
| 1 | +50° | 2.36 | 0.16 | 13.2 | 11 |
| 2 | +50° | 2.0 | 0.16 | 10.8 | 9.5 |
| 3 | +50° | 2.0 | 0.5 | 10.8 | 9.5 |
| 4 | +80° | 1.6 | 0.5 | 9.8 | 7.5 |

TABLE 2

| Compound | $I_{2S}$ (% Id tot) | I Ep | $A_{NS}$ | $A_{NA}$ (% GIN tot) | $A_{6S}$ | $A_{NH2}$ |
|---|---|---|---|---|---|---|
| 1 | 70 | — | 90 | 10 | 60 | — |
| 2 | 70 | — | 60 | 10 | 60 | 30 |
| 3 | 70 | — | 60 | 40 | 60 | — |
| 4 | 20 | 50 | 60 | 40 | 60 | — | where:
$I_{2S}$ = iduronyl-2-sulphate
I Ep = iduronyl-2,3-epoxide
$A_{NS}$ = glucosamine-N-sulphate
$A_{NA}$ = N-acetyl glucosamine
$A_{6S}$ = glucosamine 6.0-sulphate
GIN, $A_{NH2}$ = glucosamine
Id = L iduronyl acid From Tables 1 and 2 it can be seen that the epoxy derivative of heparin according to the invention has the following characteristics compared with heparide:
considerable increase in specific rotation:
reduction in sulphate/acetyl ratio;
acetyl/carboxyl ratio maintained against heparan indices;
molecular weight stability;
shift of organic sulphur content to correspond to characteristic data of heparin precursors;
low iduronyl-2,0-sulphate content.

On electrophoresis conducted in accordance with CAPPELLETTI (Anal. Biochem. 99,311(1979), the epoxy derivative shows a single band with anodic migration exceeding the starting substance.

DESCRIPTION OF THE DRAWING

The drawing shows the $^{13}C$ nuclear magnetic resonance spectra of the starting sodium heparin (FIG. 1A), of the heparide (FIG. 1B) and of the epoxy derivative of the present invention (FIG. 1C).

The spectrum for (FIG. 1C) shows the appearance of a double signal at 52 and 54 ppm (C.2 and C.3) and a signal at 98 ppm (C.1), which are characteristic of epoxy derivatives.

Figure 1A:
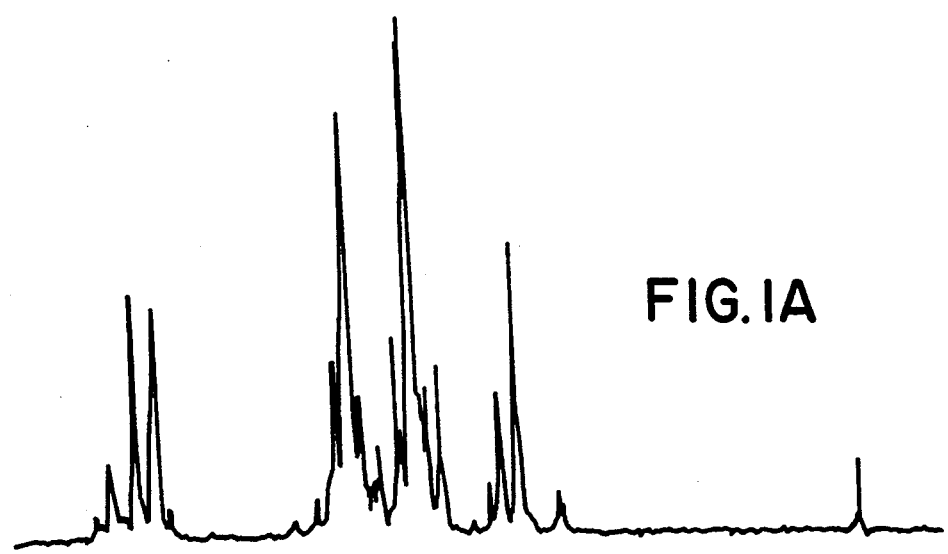
Figure 1B:
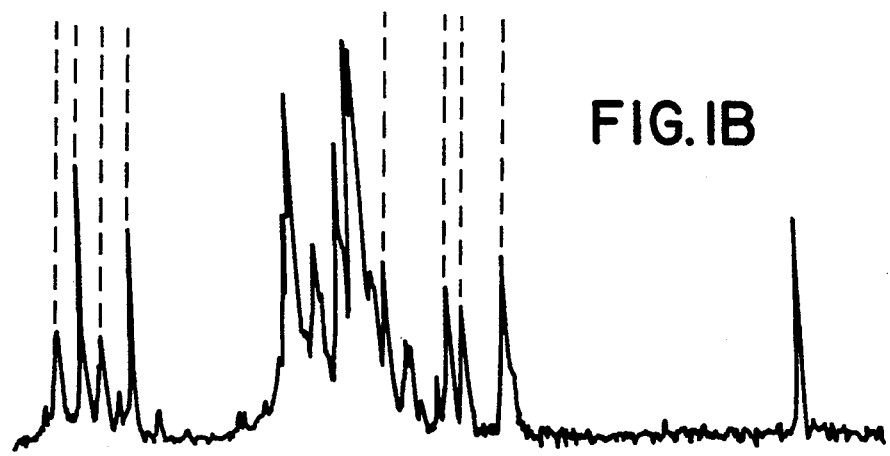
Figure 1C:
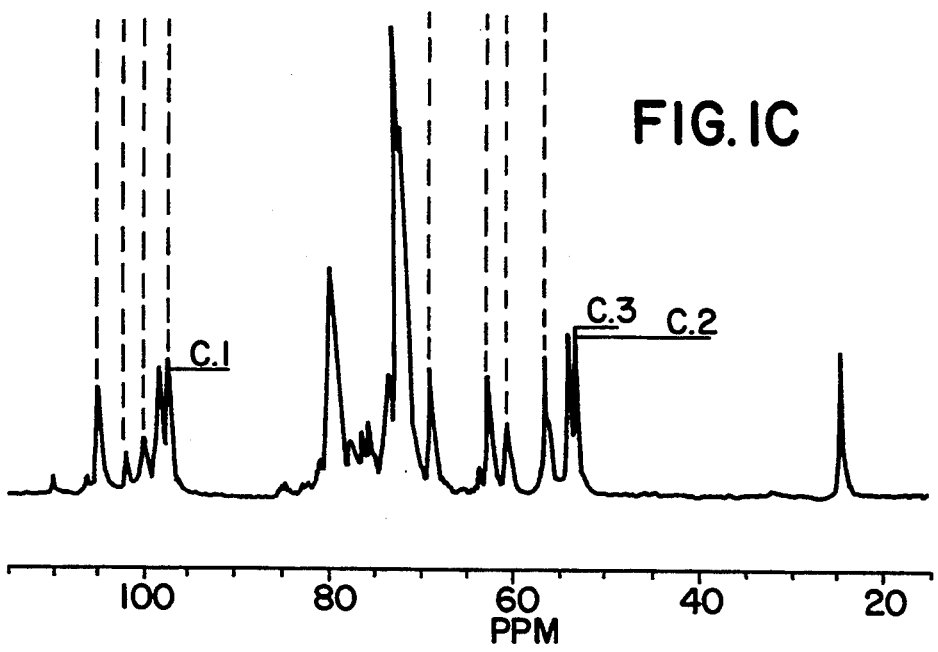

The heparin epoxy derivatives of the present invention have interesting biological and pharmacological properties, and in particular:
absence of anticoagulant activity (USP and antiXa);
fibrinolylic activity determined by the FDP test (CASTELAN, J. Clin. Path. 21,638(1969);
antithrombotic activity evaluated by the stasis method; reduction in the time of bleeding induced by cutting the tail of the rat, compared with the starting heparin;
antagonism towards reactions induced by free superoxide and hydroperoxide radicals (epinephrine auto-oxidation method).

In particular the heparin epoxy derivatives were tested in the venous thrombosis, in the arterial thrombosis and in the endothelemia.

In the venous model the activity resulted 2-3 times higher than in the others models.

The epoxy derivatives were screened for mutagenic activity in 3 strains of Salmonella typhimurium. Testing was carried out both in the absence and in the presence of a rat liver metabolic activation system (S-9) in a single experiment. The methods used in this study were essentially those of Maron and Ames (Maron-Ames - Mutation Res. 13,173,(1983).

No treatment of any of the test strains, either in the absence or presence of S-9, resulted in an increase in revertant numbers sufficient to be considered as evidence of mutation induction.

It is concluded that, in a screening assay, heparin epoxy derivatives were unable to induce mutation in Salmonella typhimurium strains TA98, TA100 and TA1535 when tested up to 5000 µg/plate in the absence and in the presence of metabolic activation.

The new epoxy derivatives were active in preventing thrombosis induced in rat by injection of KC (K. Carragenine). Its action is slightly inferior to that of UH (Unfractioned Heparin). This findings suggests that an activity other than anticoagulation is envolved in the antithrombotic activity of the epoxy derivatives.

Other studies have shown that the epoxy derivatives are interesting stimulators of tissue plasminogen activator (PA) and Catalyse Fibrinolysis at a concentration of only 5 µg/ml with optimum effect at 25 µg/ml.

The clinical effects of heparin epoxy derivatives were tested in patients affected by chronic venous failure secondary to varices or deep thrombosis.

All patients showed a deficit of fibrinolysis (low values of plasma euglobulin lytic activity (ELA)).

The epoxy derivatives were administered for 60 days (100 mg/day-oral dose).

"Strain gauge" plethysmography showed a decrease in the maximum venous capacity (MVC) both at 40 and 60 mm Hg; this is an index of reduced venous stasis and an improvement in vessel patency.

No side-effect was observed in the patients.

The heparin epoxy derivatives of the present invention can therefore be used in the preparation of pharmaceutical compositions for the therapy of thrombosis and atherosclerosis.

The pharmaceutical compositions can be prepared in forms suitable for intradermic, intramuscular, intravenous, intraocular, oral, topical and inhalatory use.

In addition, the antagonism towards free radicals means that the derivatives of the present invention can be considered also as new substances of fundamental interest in the field of progressive metabolic alterations connected with free radical biochemistry.

The following examples are given for the purposes of non-limiting illustration of the invention.

EXAMPLE 1

10 g of sodium heparin (180 U/mg USP) are dissolved in 100 ml of 0.01M HCl and the solution heated to 70° C. for 60 minutes. The solution is then cooled and neutralized with 0.01M NaOH and the product precipitated by adding 1:1 EtOH.

The precipitate is dried to obtain 8 g of partially desulphated heparin (compound A) which on analysis gave the following results: Specific rotation = +55° organic sulphur = 9.4%: sulphate/carboxyl ratio = 2.03.

8 g of said partially desulphated heparin are dissolved in 50 ml of distilled water and the solution is adjusted to pH 9.5 and kept stirring.

0.8 ml of acetic anhydride are added slowly in quantities of 0.1 ml at a time, maintaining the pH between 9.3 and 9.5 and the temperature between 25° and 28° C., after which stirring is continued for 30 minutes.

2 g of sodium chloride are added and precipitation obtained at pH 6 by adding a volume of acetone equal to the volume of solution.

The precipitate is dried to obtain 6.8 g of partially desulphated and acetylated heparin (compound B) (heparide) which on analysis gives the following results:

Specific rotation = +55°; organic sulphur = 9.2%.

6 g of heparide are dissolved in 60 ml of 0.1N NaOH, the solution is heated over a water bath to 70° C. and 0.6 ml of 37% hydrogen peroxide are added over a period of 60 minutes under slow stirring. When the addition is complete, the solution is cooled rapidly to 20° C. and then neutralized with 0.1M HCl to pH 6.

The solution is desalified through cationic-anionic resins to completely remove the sulphate ions, NaCl is added (2 parts by weight per 100 parts of solution) and the product precipitated by adding a volume of acetone equal to the volume of solution.

The precipitate is dried to obtain 5.2 g of heparide epoxide which on analysis gives the following results:

Specific rotation = +80°; organic sulphur = 7.4%; sulphate/carboxyl ratio = 1.65; NMR = double signal at 52 and 54 ppm and at 98 ppm.

EXAMPLE 2

10 g of heparin are desulphated and acetylated as in Example 1. 6 g of the product obtained are dissolved in 60 ml of distilled water, the solution adjusted to pH 13 with 2M KOH, heated to 80° C. and 0.8 ml of 37% $H_2O_2$ added dropwise over a time of 30 minutes. When the addition is complete, the solution is cooled rapidly to 25° C. and then neutralized to pH 6.

The solution is then demineralized by ultrafiltration at 600 cutoff with successive dilution and concentration, the final solution being diluted to 100 ml.

Finally, NaCl is added (2 parts by weight per 100 parts of solution) and the product precipitated by adding a volume of acetone equal to the volume of solution.

On product analysis, results similar to those of Example 1 are obtained.

EXAMPLE 3

10 g of heparin are desulphated and acetylated as in Example 1. 6 g of the product obtained are dissolved in 100 ml of distilled water, the solution heated over a water bath to 70° C., adjusted to pH 13 with 20% NaOH, and 0.6 ml of 37% $H_2O_2$ then added dropwise over a time of 1 hour while maintaining the pH at 13.

When the addition is complete, the solution is cooled rapidly to 15° C. and then neutralized to pH 6 with 1M HCl.

The solution is desalified through mixed-bed resins and the product precipitated with 2 volumes of ethanol after adding NaCl (1 part by weight per 100 parts of solution).

On product analysis, results similar to those of Example 1 are obtained.

I claim:

1. A process for preparing epoxyheparide polysaccharides of formula (I):

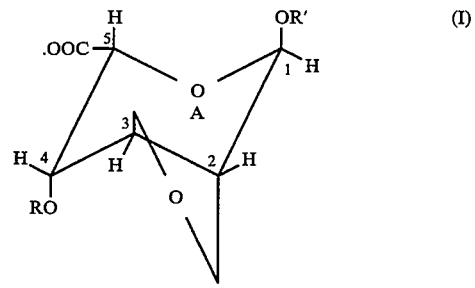

wherein A is a pyran ring with substituents 1 and 4 in the axial position and 5 in the equatorial position, and R and R' are hexosamines which constitute a polysaccharide chain bonded to said ring A by a glucoside, and one of R and R' is H when the ring A is in the terminal position of said polysaccharide chains and said heparide has a $COCH_3$ to COOH ratio of 0.5 said process comprising a) N-desulphation of heparin to obtain the corresponding heparamine;
b) acetylation of the heparamine of step (a) to obtain the corresponding heparide;
c) expoxidation of the heparide of step (b) by treating the heparide with hydrogen peroxide in an alkaline reaction medium at pH 12–14; and
d) cooling the solution obtained in step (c) to a temperature of between 15° and 25° C. and adjusting the pH to between 5.8 and 6.0.

2. Epoxy-heparide polysaccharides of formula (I):

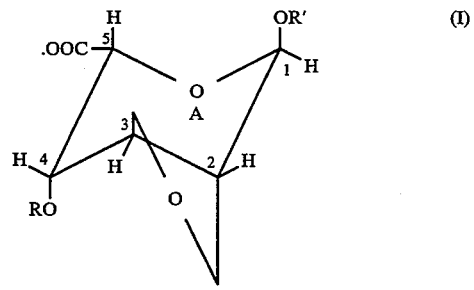

which are prepared by the process of claim 1, wherein A is a pyran ring with substituents 1 and 4 in the axial position and 5 in the equatorial position, and R and R' are hexosamines which constitute polysaccharide chains bonded to said ring A by a glucoside bond, and one of R and R' is H when said ring A is in the terminal position of said polysaccharide chains and said heparide has a $COCH_3$ to COOH ratio of 0.5.

3. A process as claimed in claim 1, wherein said alkaline reaction medium is an aqueous solution containing an alkaline substance chosen from the group consisting of NaOH, KOH and $NH_4OH$.

4. A process as claimed in claim 1, wherein said epoxidation is conducted at a temperature of between 40° and 80° C.

5. A process as claimed in claim 1, wherein said hydrogen peroxide is of 37% concentration and is added in a quantity of between 0.5 and 1 ml per 10 g of N-desulphated and acetylated heparin over a time of between 1 and 4 hours.

6. Pharmaceutical composition for the therapy of human thrombosis and atherosclerosis, said pharmaceutical composition comprising effective amounts for the treatment of atherosclerosis and thrombosis of epoxy-heparide polysaccharides of formula (I)

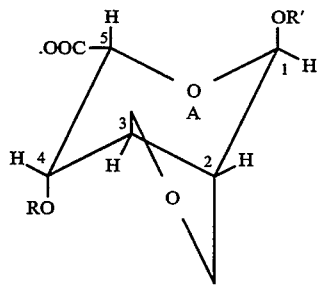

which are prepared by the process of claim 1, wherein A is a pyran ring with substituents 1 and 4 in the axial position and 5 in the equatorial position, and R and R' are hexosamines which constitute polysaccharide chains bonded to the ring A by a glucoside bond, and one of R and R' is H when the ring A is in the terminal position of said polysaccharide chains, said heparide having a COCH$_3$ to COOH ratio of 0.5, and a pharmaceutically acceptable diluent.

7. Therapeutic method for the treatment of human thrombosis and atherosclerosis consisting in the administration to a human in need of such treatment of an effective amount for the treatment of atherosclerosis and thrombosis of epoxy-heparide polysaccharides of formula (I)

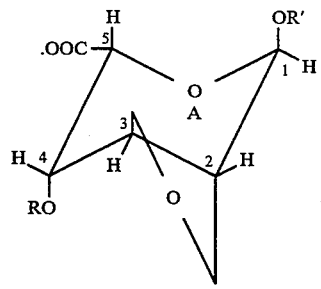

which are prepared by the process of claim 1, wherein A is a pyran ring with substituents 1 and 4 in the axial position and 5 in the equatorial position, and R and R' are hexosamines which constitute polysaccharide chains bonded to the ring A by a glucoside bond, and one of R and R' is H when the ring A is in the terminal position of said polysaccharide chains, said heparide having a COCH$_3$ to COOH ratio of 0.5.

8. Therapeutic method according to claim 7, comprising administration of 100 mg/day of epoxy heparide polysaccharides of formula (I) which are prepared by the process of claim 1.

9. Therapeutic method according to claim 8 wherein a human thrombosis is treated.

10. Therapeutic method according to claim 8 wherein atherosclerosis is treated.

11. A composition as defined in claim 6 wherein the effective amount is 100 mg.

12. A method as defined in claim 7 wherein the effective amount is 100 mg/day.

* * * * *